United States Patent [19]

Minoguchi et al.

[11] Patent Number: 5,225,430
[45] Date of Patent: Jul. 6, 1993

[54] AZOLYLMETHYLOXABICYCLOHEXANE DERIVATIVES AND FUNGICIDAL COMPOSITIONS THEREOF

[75] Inventors: Masanori Minoguchi, Kiyose; Satoru Kumazawa, Iwaki, both of Japan

[73] Assignee: Kureha Kagahu Kogyo K.K., Tokyo, Japan

[21] Appl. No.: 798,716

[22] Filed: Nov. 29, 1991

[30] Foreign Application Priority Data

Nov. 30, 1990 [JP] Japan ............................ 2-329647
Oct. 31, 1991 [JP] Japan ............................ 3-313758

[51] Int. Cl.$^5$ ............... A01N 43/653; C07D 249/08; C07D 405/06.
[52] U.S. Cl. ................. 514/383; 548/262.2; 548/267.2; 548/267.4; 548/268.8
[58] Field of Search ............ 514/383; 548/262.2, 548/267.2, 267.4, 268.8

[56] References Cited

U.S. PATENT DOCUMENTS 4,863,505 9/1989 Kumazawa et al. ............ 71/92
4,938,792 7/1990 Kumazawa et al. ............ 71/92

FOREIGN PATENT DOCUMENTS 0267778 5/1988 European Pat. Off. .
0329397 2/1989 European Pat. Off. .
0357404 8/1989 European Pat. Off. .
62-149667 7/1987 Japan .
1-93574 4/1988 Japan .
1-301664 12/1989 Japan .
2-85259 3/1990 Japan .

*Primary Examiner*—Patricia L. Morris
*Attorney, Agent, or Firm*—Lowe, Price, LeBlanc & Becker

[57] ABSTRACT

Disclosed herein is a process for preparing a cis-azole derivative represented by the general formula (I)

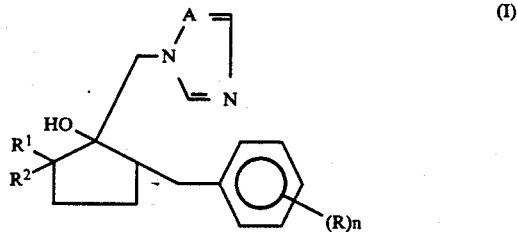

wherein $R^1$ and $R^2$ denote each a hydrogen atom or an alkyl group, R denotes a halogen atom, a nitro group, a cyano group, an alkyl group, a haloalkyl group or a phenyl group, A denotes a nitrogen atom or a methine group, and n stands for an integer of 1–5, which comprises reducing an azolylmethyloxabicyclohexane derivative represented by the general formula (VI)

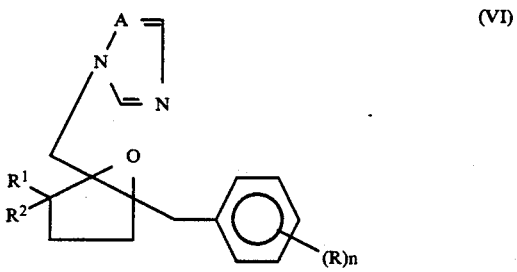

wherein $R^1$, $R^2$, R, A and n have the same meanings as defined above. A fungicidal composition comprising the azolylmethyloxabicyclohexane derivative represented by the above-mentioned general formula (VI) is also desclosed.

7 Claims, No Drawings

AZOLYLMETHYLOXABICYCLOHEXANE DERIVATIVES AND FUNGICIDAL COMPOSITIONS THEREOF

BACKGROUND OF THE INVENTION

1.) Field of the Invention

The present invention relates to a process for selectively preparing racemic or optically active cis-azole derivatives which are active ingredients of agricultural and horticultural compositions, and to intermediates for preparing the azole derivatives, a process for preparation thereof, and fungicidal compositions.

2) Description of the Related Art

Azole derivatives represented by the following general formula (I) have heretofore been known to have excellent agricultural and horticultural fungicidal effects and plant growth controlling effects, and a process for preparation thereof has been known too.

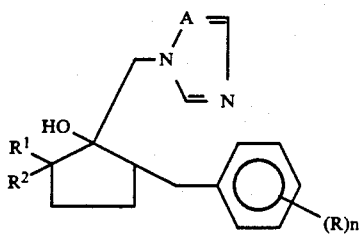

wherein $R^1$ and $R^2$ mean a hydrogen atom or an alkyl group, independently, R denotes a halogen atom, a nitro group, independently, R denotes a halogen atom, a nitro group, a cyano group, an alkyl group, a haloalkyl group or a phenyl group, A denotes a nitrogen atom or a methine group, and n stands for 0 or an integer of 1-5.

Namely, EP-A-329397 discloses a process for preparation of a racemic mixture of cis-azole derivatives and trans-azole derivatives represented by the above general formula (I), and EP-A-267778 discloses a process for preparation of cis- or trans-azole derivatives represented by the general formula (I′)

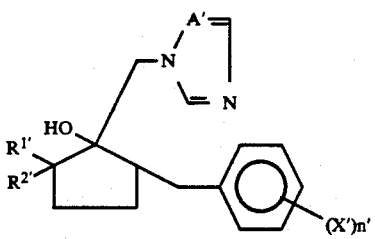

wherein $R^{1'}$ and $R^{2'}$ denote each a $C_1$–$C_5$ alkyl group or a hydrogen atom, but $R^{1'}$ and $R^{2'}$ are not hydrogen atom at the same time, X′ denotes a halogen atom, a $C_1$–$C_5$ alkyl group or a phenyl group, n′ stands for 0 or an integer of 1 or 2, and A′ denotes a nitrogen atom or a methine group, which comprises using cis- or trans-oxaspiroheptane derivatives represented by the general formula (II′)

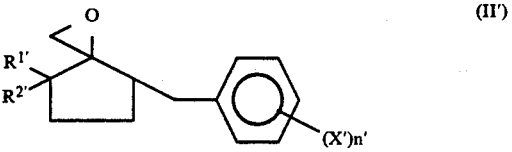

wherein $R^{1'}$ and $R^{2'}$, X′ and n have the same meanings as defined above.

It has been known that the azole derivatives represented by the general formula (I) has a higher activity in the cis form than in the trans form.

It is therefore desired to provide a process by which cis-form azole derivatives represented by the general formula (I) having a higher fungicidal activity are selectively prepared. In the process described in EP-A-329397, however, since a mixture of cis form and tans form is prepared, the yield of the cis form is reduced under the influence of the by-produced trans form and it is necessary to separate the cis-azole derivatives from the mixture of the cis form and trans form. Further, in the process described in Japanese Patent Application Laid-Open No. 93574/1989, a process for separating the cis form is required in a stage of preparing oxaspiroheptane derivatives represented by the general formula (II′) in order to obtain the cis azole derivatives.

As be described above, the prior processes require a separation step for obtaining purified cis form. In the separation step, large amounts of column packings or solvents are used and a loss is caused when separation is carried out. Accordingly, it is not advantageous to combine the separation step in the indusutrial process for preparation of the cis form.

The present invention has been achieved in the light of the above described circumstances in the prior arts.

SUMMARY OF THE INVENTION

An object of the present invention is therefore to provide a process for selectively preparing cis-azole derivatives represented by the general formula (I) which show reliable effects in a smaller amount because of having a high fungicidal activity, by which the amount existent in the environment becomes small.

Another object of the present invention is to provide intermediates useful for producing the cis-azole derivatives A further object of the present invention is to provide processes for preparation of the intermediates.

A still further object of the present invention is to provide a fungicidal composition.

The present inventors have noticed the fact that the cis-azole derivatives represented by the general formula (I) has a higher effectiveness as compared with trans-azole derivatives which are geometrical isomers. As a result of earnest studies concerning the process for selective preparation in order to solve the above mentioned problems, it has found a process by which only cis form can be prepared, leading to completion of this invention.

With respect to configuration of the azole derivatives represented by the general formula (I) in the present specification, cis form means those wherein a substituted or non-substituted phenylmethyl group is bonded to the cis position of the hydroxyl group attached on the cyclopentane ring, and trans form means those wherein said group is bonded to the trans position of the hydroxyl group attached on the cyclopentane ring.

The characteristic of the present invention is as follows.

In one aspect of this invention, there is thus provided a process for preparing a cis-azole derivatives represented by the general formula (I)

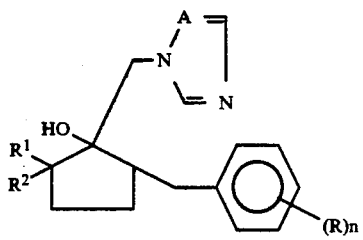
(I)

wherein $R^1$ and $R^2$ denotes each a hydrogen atom or an alkyl group, R denotes a halogen atom, a nitro group, a cyano group, an alkyl group, a haloalkyl group or a phenyl group, A denotes a nitrogen atom or a methine group, and n stands for 0 or an integer of 1–5, which comprises subjecting an oxaspiroheptane derivative represented by the general formula (II) to a rearrangement reaction

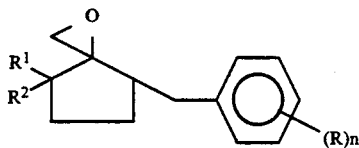
(II)

wherein $R^1$, $R^2$, R, and n have the same meanings as defined above,
epoxidating the resultant cyclopentenemethanol derivative represented by the general formula (III)

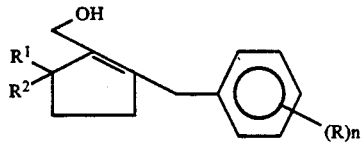
(III)

wherein $R^1$, $R^2$, R, and n have the same meanings as defined above,
conducting sulfonic esterification of the resultant oxabicyclohexanemetanol derivative represented by the general formula (IV)

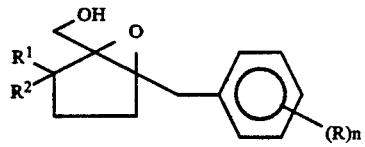
(IV)

wherein $R^1$, $R^2$, R, and n have the same meanings as defined above,
sujecting to a substitution reaction the resultant oxabicyclohexanemethanol sulfonic acid ester derivative represented by the general formula (V) with a 1,2,4-triazole or imidazole

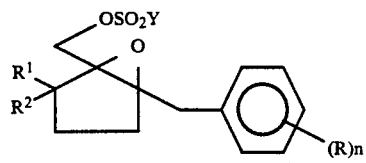
(V)

wherein $R^1$, $R^2$, R, and n have the same meanings as defined above, and Y denotes an alkyl group or a nonsubstituted or substituted phenyl group,
and reducing the resultant azolylmethyloxabicyclohexane derivative represented by the general formula (VI)

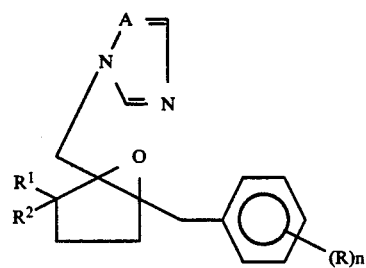
(VI)

wherein $R^1$, $R^2$, R, A and n have the same meanings as defined above.

In another aspect of this invention, there is also provided a process for preparing a cis-azole derivatives represented by the above-mentioned general formula (I) which comprises reducing an azolylmethyloxabicyclohexane derivative represented by the general formula (VI)

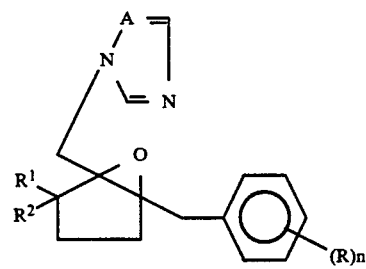
(VI)

wherein $R^1$, $R^2$, R, A and n have the same meanings as defined above.

In a further aspect of this invention, there is also provided an azolylmethyloxabicyclohexane derivative represented by the general formula (VI)

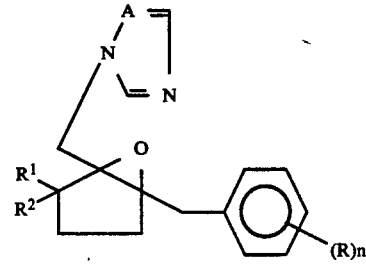
(VI)

wherein $R^1$, $R^2$, R, A and n have the same meanings as defined above.

In a further aspect of this invention, there is also provided a process for preparing an azolylmethyloxabicyclohexane derivative represented by the above described general formula (VI) which comprises sujecting to a substitution reaction an oxabicyclohexanemethanol sulfonic acid ester derivative represented by the general formula (V) with a 1,2,4-triazole or an imidazole.

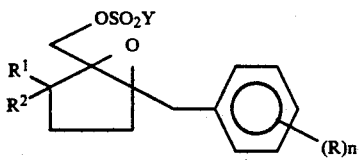 (V)

wherein $R^1$, $R^2$, R, and n have the same meanings as defined above, and Y denotes an alkyl group or a non-substituted or substituted phenyl group.

In a further aspect of this invention, there is also provided an oxabicyclohexanemetanol sulfonic acid ester derivative represented by the general formula (V)

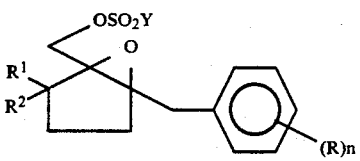 (V)

wherein $R^1$, $R^2$, R, n and Y have the same meanings as defined above.

In a further aspect of this invention, there is also provided a process for preparing an oxabicyclohexanemetanol sulfonic acid ester derivatives represented by the above described formula (V) which comprises conducting sulfonic esterification of an oxabicyclohexanemethanol derivative represented by the general formula (IV)

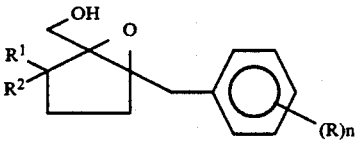 (IV)

wherein $R^1$, $R^2$, R, and n have the same meanings as defined above.

In a further aspect of this invention, there is also provided an optically active oxabicyclohexanemethanol deirvative represented by the general formula (IV)

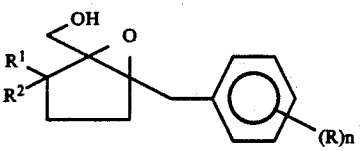 (IV)

wherein $R^1$, $R^2$, R, and n have the same meanings as defined above.

In a further aspect of this invention, there is also provided a process for preparing an oxabicyclohexanemethanol derivative represented by the above described general formula (IV) which comprises epoxidating a cyclopentenemethanol derivative represented by the general formula (III)

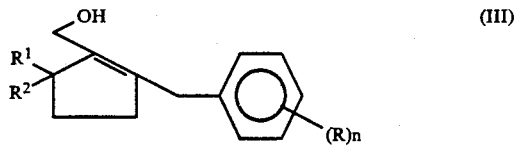 (III)

wherein $R^1$, $R^2$, R, and n have the same meanings as defined above.

In a further aspect of this invention, there is also provided a cyclopentenemethanol deirvative represented by the general formula (III)

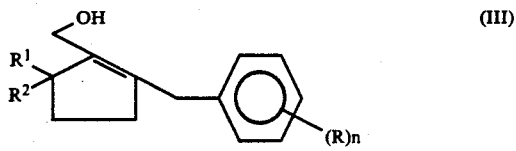 (III)

wherein $R^1$, $R^2$, R, and n have the same meanings as defined above.

In a further aspect of this invention, there is also provided a process for preparing a cyclopentenemethanol derivative represented by the above described general formula (III) which comprises subjecting an oxaspiroheptane derivative represented by the general formula (II) to a rearrangement reaction

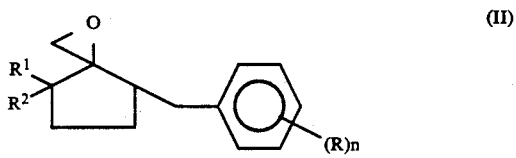 (II)

wherein $R^1$, $R^2$, R, and n have the same meanings as defined above.

In a still further aspect of this invention, there is also provided a fungicidal composition comprising as an effective ingredient an azolylmethyloxabicyclo-hexane derivative represented by the following formula (VI) together with an inert carrier or adjuvants;

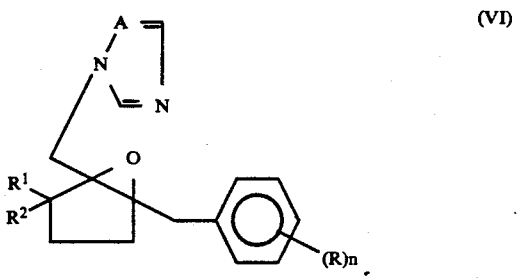 (VI)

wherein $R^1$, $R^2$, R, A and n have the same meanings as defined above.

DETAILED DESCRIPTION OF PREFERRED EMBODIMENTS

The process for preparing the cis-azole derivative represented by the above described general formula (I) is shown as the following reaction formulas.

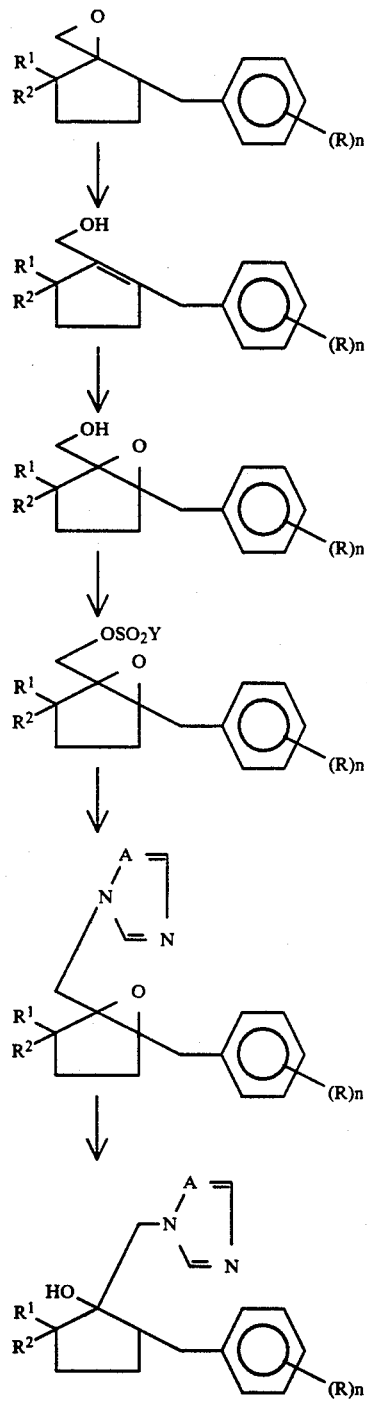

In the following, the present invention will be illustrated in greater detail.

The cis-azole derivative represented by the general formula (I) and intermediates thereof of the present invention will be first explained. In the azole derivatives represented by the above-mentioned general formula (I), $R^1$ and $R^2$ mean a hydrogen atom or an alkyl group, and preferably a hydrogen atom or an $C_1$-$C_3$ alkyl group. R means a halogen atom, a nitro group, a cyano group, an alkyl group, a haloalkyl group or a phenyl group, and preferably a chlorine atom bonded to the 4-position.

n is 0 or an integer or from 1 to 5 and preferably 0–1.
A means a nitrogen atom or a methine group.

In the intermediates represented by the above-mentioned general formulas (II), (III), (IV), (V) and (VI), the substituents $R^1$, $R^2$ and R, n and A have the same meanings as those in the azole derivative represented by the general formula (I), and preferred embodiments are also the same. In the oxabicyclohexanemethanol sulfonic acid ester derivative represented by the general formula (V), Y means an alkyl group or a non-substituted or substituted phenyl group, and preferably a $C_1$-$C_4$ alkyl group, a phenyl group or a p-methylphenyl group. The process of the present invention will be explained in the following in accordance with the above-mentioned reaction formulas Rearrangement Reaction The oxaspiroheptane derivative represented by the general formula (II) can be changed into the cyclopentene methanol derivatives represented by the general formula (III) by a rearrangement reaction in a presence of an acid catalyst in an organic solvent at a reaction temperature in a range of from 0° C. to 40° C. for a reaction time in a range of from 1 hour to 5 hours. As the organic solvent, ethers can be used. Particularly preferred examples include dioxane, tetrahydrofuran (THF) and diethyl ether. As the acid catalyst, it is possible to use, for example, sulfuric acid, hydrochloric acid, $AlCl_3$, $BF_3$ and the like.

Epoxidation Reaction

The oxabicyclohexanemethanol derivative represented by the general formula (IV) is obtained by epoxidation of the cyclopentenemethanol derivative represented by the general formula (III) using an inorganic or organic peroxide in an organic solvent at a reaction temperature in a range of from $-78°$ C. to 25° C. for a reaction time in a range of from 1 hour to 5 hours.

Examples of the organic solvents include alkyl halides such as dichloromethane or dichloroethane etc., aromatic hydrocarbons such as toluene etc., aliphatic hydrocarbons such as hexane, heptane or isooctane etc. As the peroxide, it is possible to use metachloroperbenzoic acid, cumene hydroperoxide and tertiary butyl hydroperoxide and the like.

Furthermore, when the epoxidation is carried out using an asymmetric reagent, it is possible to obtain an optically active oxabicyclohexanemethanol derivative represented by the general formula (IV). For example, an optically active (+)-oxabicyclohexanemethanol derivative represented by the general formula (IV) can be obtained by carrying out the epoxidation reaction using as an asymmetric reagent a combination of (2R,3R)-(+)-diethyl tartarate and titanium tetraisopropoxide. Likewise, an optically active (−)-oxabicyclohexanemethanol derivative represented by the general formula (IV) can be obtained by carrying out the epoxidation reaction using as an asymmetric reagent a combination of (2S,3S)-(−)-diethyl tartarate and titanium tetraisopropoxide.

In such cases, the above-mentioned combination of the reagents can be used together with Molecular seives.

Using the thus resulted optically active oxabicyclohexanemethanol derivative represented by the general fromula (IV), the optically active cis-azole derivative represented by the general formula (I) can be prepared by the sulfonic esterification, the azolation reaction and the reduction reaction in accordance with the above-mentioned chemical formulas as follows.

Sulfonic Esterification Reaction

The oxabicyclohexanemethanol sulfonic acid ester derivatives can be obtained by subjecting the oxabicyclohexanemethanol derivative represented by the general formula (V) to sulfonic esterification in an organic solvent using benzenesulfonyl chloride, substituted benzenesulfonyl chloride or alkanesulfonyl chloride and a hydrochloric acid binding agent at a reaction temperature in a range of from 0° C. to 40° C. for a reaction time in a range of from 0.5 hours to 5 hours.

A preferred example of the substituted benzenesulfonyl chloride is p-methylbenzenesulfonyl chloride, and a preferred example of the alkanesulfonyl chloride is methanesulfonyl chloride.

Examples of the hydrochloric acid binding agent include trimethylamine, triethylamine, N,N-dimethylaniline and N,N-diethylaniline, etc., but the present invention is not limited to using them.

Examples of the organic solvent include aromatic hydrocarbons such as benzene, toluene and xylene, etc., aliphatic hydrocarbons such as hexane, heptane and isooctane etc., alkyl halides such as dichlorometane, chloroform, carbon tetrachloride and dichloroethane, etc., and ethers such as dioxane, THF and diethyl ether etc.

Azolation Reaction

The azolylmethyloxabicyclohexane derivative represented by the general formula (VI) can be obtained by reacting the oxabicyclohexanemethanol sulfonic acid ester represented by the general formula (V) with a 1,2,4-triazole or an imidazole, and a base compound in an organic solvent at a reaction temperature in a range of from 0° C. to 100 ° C. for a reaction period in a range of from 1 hour to 5 hours to substitute a $YSO_2$ O group with an azole ring.

As the base compound, sodium hydride may be preferably used.

Preferred example Of the Organic solvent used in this reaction step include aromatic hydrocarbons such as benzene, toluene and xylene etc., aliphatic hydrocarbons such as hexane, heptane and isooctane, etc., alkyl halides such as dichloromethane, chloroform, carbon tetrachloride and dichloroethane etc., ethers such as dioxane, THF and diethyl ether, etc., alcohols such as methyl alcohol, ethyl alcohol, etc., and polar aprotic solvents such as acetonitrile, acetone, DMF, DMSO and N-methylpyrrolidone etc.

Reduction Reaction

The cis-azole derivative represented by the general formula (I) can be obtained by reducing the azolylmethyloxabicyclohexane derivatives in an ether using a metal hydride or a combination of metal hydride and Lewis acid at a reaction temperature in a range of from 0° C. to 100° C. for a reaction period in a range of from 0.5 hours to 5 hours.

Examples of the ethers used in this reaction step include diethyl ether, THF and diglym. As the metal hydride, lithium aluminium hydride may be preferably used. An example of the Lewis acid used together with the metal hydride is $AlCl_3$.

According to the process of the present invention, cis-azole derivatives represented by the above mentioned general formula (I) which show reliable effects in a smaller amount because of having a higher activity, by which the amount existent in the environment becomes small, can be selectively prepared.

As a result of studies by the present inventors about the use, it has been found that the above-mentioned azolylmethyloxabicyclohexane represented by the general formula (VI) can be used as fungicides in addition to as the intermediate.

In the following, use of the azolylmethyloxabicyclohexane derivative represented by the formula

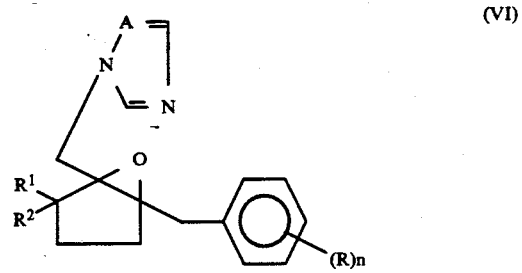

wherein $R^1$, $R^2$, R, A and n have the same meanings as defined above.

When the azolylmethyloxabicyclohexane derivative represented by the formula (VI) (referred to as "compound of this invention", hereinafter) is used as a fungicidal composition, it is generally used in the form of dust, wettable powder, granules, emulsion and the like together with carriers or other adjuvants. In such a case, the preparations are prepared so as to contain one or more of the compound of this invention in an amount of 0.1%-95% by weight, preferably, 0.5%-90% by weight, and more preferably 2%-70% by weight.

Examples of carriers, diluents and surfactants used as the adjuvants for preparations include the following.

Examples of solid carriers include talc, kaolin, bentonite, diatomaceous earth, white carbon and clay, etc.

Examples of liquid carriers (diluents) include water, xylene, toluene, chlorobenzene, cyclohexane, cyclohexanone, dimethylsulfoxide, dimethylformamide and alcohol, etc.

Examples of the surfactants include polyoxyethylene alkylaryl ether and polyoxyethylene sorbitan monolaurylate etc., as emulsifiers; lignin sulfonates, dibutylnaphthalenesulfonates, etc., as dispersing agents; and alkylsulfonates and alkylphenylsulfonates, etc., as wetting agents.

The above preparations are classified into those which can be used directly, and those which are used after diluting so as to have a suitable concentration with a diluent such as water, etc.

The concentration of the present compounds in case of using after diluting is preferred to be in a range of 0.001%-1.0%.

Further, the application dosage of the compound of this invention is in a range of 20 g-5000 g and preferably 50 g -1000 g per 1 ha of agricultural and horticultural land such as farm, paddy field, fruit garden, hothouse, etc.

It is of course possible to increase and decrease the concentration and the application dosage beyond the above-mentioned ranges, because they depend upon the form of preparations, method of application, place to be used, target crops, etc.

Furthermore, the compound of this invention can be used in combination with other effective ingredients, such as other fungicides, insectcides, miticides, herbicides, etc.

EXAMPLES

Preparation examples, formulation examples and test examples are described in the following, by which the present invention is illustrated in detail.

Preparation examples 6 and 10 and Preparation examples 14, 15, 16, 17 and 18 in the exmples relates to preparation of optically active epoxyalcohol derivatives.

Preparation examples 14–18 disclose the process in which a reagent for asymmetric epoxidation is used together with Molecular Sieves.

Further, the following abbreviations and chemical formulas are used in Preparation examples 6, 10, 14, 15, 16, 17 and 18.

| (2R,3R)-(+)-diethyl tartarate | (+)-DET |
|---|---|
| (2S,3S)-(−)-diethyl tartarate | (−)-DET |
| Titanium tetraisopropoxide | Ti(O i-Pr)$_4$ |
| tert-Butylhydroperoxide | TBHP |

Enantiomer excess ratio (% ee) described in Preparation examples 6, 9, 10, 13, 14, 15, 16, 17 and 18 was determined by high performance liquid chromatography equipped with an optically active column (CHIRALCEL OK, produced by Daicel Co.)

PREPARATION EXAMPLE 1

Cyclopentene methanol derivative [Formula (III): $R^1 = R^2 = CH_3$, $(R)_n = 4\text{-Cl}$]

Preparation of 2-[(4-chlorophenyl)methyl]-5,5-dimethyl-1-cyclopentene-1-methanol:

To 20 g (0.08 mol) of 7-[(4-chlorophenyl)methyl]-4,4-dimethyl-1-oxaspiro[2.4]heptane [Formula(II): $R^1 = R^2 = CH_3$, $(R)_n = 4\text{-Cl}$] was added 150 ml of dioxane, and 5 ml of 10% sulfuric acid was added thereto with stirring under room temperature. The mixture was then stirred at room temperature for 2 hours.

The reaction solution was poured into a saturated aqueous solution of sodium hydrogen carbonate, followed by extracting with ethyl acetate. The resultant organic layer was washed with saturated aqueous saline solution.

After dried with anhydrous sodium sulfate, the organic layer was concentrated under reduced pressure to yield 17.22 g of a yellowish oily product.

The resultant product was purified by chromatography on a column of silica gel to obtain 13.16 g (0.052 mmol) of 2-[(4-chlorophenyl)methyl]-5,5-dimethyl-1-cyclopentene-1-methanol [Formula (III): $R^1 = R^2 = CH_3,(R)_n = 4\text{-Cl}$] as a colorless transparent oily product.

Yield: 65.8%.

Colorless transparent oil $^1$H NMR(CDCl$_3$); δ 1.10(s,6H),1.40–1.83(m,2H),1.97–2.33(m,2H),3.43(s,2H), 4.22(s,2H),7.03(d,2H,J=8 Hz),7.23(d,2H,J=8 Hz) IR(neat, νmax); 3350, 2950, 2850, 1490, 1408, 1360, 1090, 1012, 990, 840 cm$^{-1}$

PREPARATION EXAMPLE 2

Oxabicyclohexanemethanol derivative [Formula (IV): $R^1 = R^2 = CH_3,(R)_n = 4\text{-Cl}$]

Preparation of 5-[(4-chlorophenyl)methyl]-2,2-dimethyl-6-oxabicyclo[3.1.0]hexane-1-methanol:

10.06 g (0.04 mol) of 2-[(4-chlorophenyl)methyl]5,5-dimethyl-1-cyclopentene-1-methanol [Formula (III): $R^1=R^2=CH_3,(R)_n=4\text{-Cl}$] were dissolved in 100 ml of chloroform, followed by adding 8.08 g (0.048 mol) of metachloroperbenzoic acid with stirring under cooling with ice.

The mixture was then stirred at room temperature for 1 hour. To the reaction solution was added 7.4 g (0.1 mol) of calcium hydroxide, and the formed precipitate was removed by filtration. The chloroform layer was washed with a saturated aqueous saline solution.

After the chloroform layer was dried with anhydrous sodium sulfate, it was concentrated under reduced pressure to yield 11.86 g of light-yellowish oily product.

The resultant product was purified by chromatography on a column of silica gel to obtain 10.21 g (0.038 mmol) of 5-[(4-chlorophenyl)methyl]-2,2-dimethyl-6-oxabicyclo[3.1.0]hexane-1-methanol [Formula (IV): $R^1 = R^2 = CH_3,(R)_n = 4\text{-Cl}$]

Yield: 95%

White crystal, m.p.: 37°–39° C.

$^1$H NMR(CDCl$_3$); δ 0.9(s,3H),1.10(s,3H),1.0–1.83(m,4H),2.43(brs,1H,OH), 3.0(s,2H), 3.8(d,1H,J=12 Hz),4.1(d,1H,J=12 Hz),7.13(m,4H)

IR(KBr, νmax); 3400, 2950, 2850, 1482, 1360, 1082, 1010, 836, 780 cm$^{-1}$

PREPARATION EXAMPLE 3

Oxabicyclohexanemethanol sulfonic acid ester derivative [Formula (V): $R^1 = R^2 = CH_3,(R)_n = 4\text{-Cl}, Y = CH_3$]

Preparation of 5-[(4-chlorophenyl)methyl]-2,2-dimethyl-6-oxabicyclo[3.1.0]hexane-1-methanol methanesulfonic acid ester:

1.33 g (5 mmol) of 5-[(4-chlorophenyl)methyl]-2,2-dimethyl-6-oxabicyclo[3.1.0]hexane-1-methanol were dissolved in 10 ml of dichloromethane, followed by adding thereto 0.63 g (5.5 mmol) of methanesulfonyl chloride and 0.55 g (5.65 mmol) of triethylamine with stirring under cooling with ice.

The mixture was then stirred under cooling with ice for 1 hour. After conclusion of the reaction was confirmed by TLC, the reaction solution was poured into water and extracted with dichlorometane. The resultant organic layer was washed with aqueous solution of saturated sodium hydrogen carbonate and aqueous saline solution.

After dried with anhydrous sodium sulfate, the organic layer was concentrated under reduced pressure to yield 1.86 g of a light-yellowish oily product.

The resultant product was purified by chromatography on a column of silica gel to obtain 1.57 g (4.55 mmol) of 5-[(4-chlorophenyl)methyl-2,2-dimethyl-6-oxabicyclo[3.1.0]hexane-1-methanol methanesulfonic acid ester [Formula (V): $R^1 = R^2 = CH_3,(R)_n = 4\text{-Cl}, Y=CH_3$]

Yield: 91%

White crystal, m.p. 78.5°–79.0° C.

$^1$H NMR (CDCl$_3$); δ 0.98(s,3H),1.10(s,3H),0.83–2.0(m,4H),2.93(s,2H),3.07 (s,3H),4.37(d,1H,J=12 Hz),4.70(d,1H,J=12 Hz),7.07(d,2H,J=8 Hz), 7.25(d,2H,J=8 Hz)

IR(KBr, νmax); 3000, 2940, 2850, 1480, 1350, 1162, 1080, 944, 810 cm$^{-1}$

PREPARATION EXAMPLE 4

Azolylmethyloxabicyclohexane derivative [Formula(VI): $R^1 = R^2 = CH_3$, $(R)_n = 4\text{-Cl}$, $A = N$]

Preparation of 5-[(4-chlorophenyl)methyl]-2,2-dimethyl-1-(1H-1,2,4-triazol-1-ylmethyl)-6-oxabicyclo[3.1.0]hexane (Compound No. VI-1):

To 0.42 g (10.5 mmol) of oily 60% sodium hydride washed with hexane was added 15 ml of dimethylformamide (DMF) and stirred at room temperature. 0.73 g (10.56 mmol) of 1,2,4-triazole were then added thereto. After the mixture was stirred for 30 minutes, 5 ml of a DMF solution containing 3.05 g (8.8 mmol) of 5-[(4-chlorophenyl)methyl]-2,2-dimethyl-6-oxabicyclo[3.1.0]hexane-1-methanol methanesulfonic acid ester [Formula (V): $R^1 = R^2 = CH_3$, $(R)_n = 4\text{-Cl}$, $Y = CH_3$] was added dropwise thereto.

Thereafter, the mixture was stirred at room temperature for 4 hours and at 40° C. for 4 hours, and the reaction solution was poured into ice water, followed by extracting with ethyl acetate. The resultant organic layer was washed with 1N-hydrochloric acid, saturated aqueous solution of sodium hydrogen carbonate and saturated aqueous saline solution. After dried with anhydrous sodium sulfate, the organic layer was concentrated under reduced pressure to yield 2.88 g of a light-yellowish oily product.

The resultant oily product was purified by chromatography on a column of silica gel, followed by crystallizing with hexane to obtain 2.71 g (8.5 mmol) of 5-[(4-chlorophenyl)methyl]-2,2-dimethyl-1-(1H-1,2,4-triazol-1-ylmethyl)-6-oxabicyclo[3.1.0]hexane as white crystal [Formula (VI): $R^1 = R^2 = CH_3$, $(R)_n = 4\text{-Cl}$, $A = N$].

Yield: 96.6%

White crystal, m.p. 101.5°–102.5° C.

$^1H$ NMR(CDCl$_3$); δ0.73(s,3H),1.0(s,3H), 0.83–2.17(m,4H),2.93(s,2H), 3.07(s,3H),4.33(d,1H,J=16 Hz),4.87(d,1H,J=16 Hz), 7.17(d,2H, J=8 Hz),7.33(d,2H,J=8 Hz),7.93(s,1H),8.33(s,1H)

IR(KBr, νmax); 3100, 2940, 2850, 1480, 1420, 1260, 1200, 1130, 1084, 1020, 950, 840, 720, 660 cm$^{-1}$ With the same procedure as preparation example 4, except using an imidazole in stead of a 1,2,4-triazole, 5-[(4-chlorophenyl)methyl]-2,2-dimethyl-1-(1H-imidazol-1-ylmethyl)-6-oxabicyclo[3.1.0]hexane (Compound No. VI-2) can be prepared.

PREPARATION EXAMPLE 5

Cis-azole derivative [Formula (I): $R^1 = R^2 = CH_3$, $(R)_n = 4\text{-Cl}$, $A = N$]

Preparation of cis-5-[(4-chlorophenyl)methyl]-2,2-dimethyl-1-(1H-1,2,4-triazol-1-ylmethyl)cyclopentanol:

To 210 mg (1.57 mmol) of aluminium chloride was added 5 ml of dimethoxyethane (DME) and stirred at room temperature. To the mixutre was added 178.7 mg (4.71 mmol) of lithium aluminium hydride and stirred for 30 minutes with elevating the temperature to 50°C. 500 mg (1.57 mmol) of 5-[(4-chlorophenyl)methyl-2,2-dimethyl-1-(1H-1,2,4-triazol-1-ylmethyl)-6-oxabicyclo[3.1.0]hexane [Formula (VI): $R^1 = R^2 = CH_3$, $(R)_n = 4\text{-Cl}$, $A = N$] was added to the mixture and stirred at 50° C. for 1 hour.

The reaction solution was poured into 50 ml of ice water and extracted with ethyl acetate. The separated organic layer was washed with saturated aqueous saline solution. After dried with anhydrous sodium sulfate, the organic layer was concentrated under reduced pressure to yield 580 mg of a yellowish oily product.

The resultant oily product was isolated and purified by chromatography on a column of silica gel to obtain 280.3 mg (0.88 mmol) of cis-5-[(4-chlorophenyl)methyl]-2,2-dimethyl-1-(1H-1,2,4-triazol-1-ylmethyl)cyclopentanol [Formula (I): $R^1 = R^2 = CH_3$, $(R)_n = 4\text{-Cl}$, $A = N$].

Yield: 55.4%

White crystal, m.p. 113°–114° C.

$^1H$ NMR(CDCl$_3$); δ 0.60(s,3H),1.00(s,3H),1.07–1.90(m,5H),2.33(bs,2H), 3.53(s,1H),4.13(s,2H),7.06(d,2H,J=8 Hz),7.25(d,2H,J=8 Hz), 8.02(s,1H),8.25(s,1H)

IR(KBr, νmax); 3250, 2940, 2850, 1480, 1380, 1262, 1200, 1124, 1080, 1002, 840, 800, 720, 670 cm$^{-1}$ With the same procedure as preparation example 5, except using the compound (VI-2) instead of the compound (VI-1), cis-5-[(4-chlorophenyl)methyl-2,2-dimethyl-1-(1H-imidazol-1-ylmethyl)cyclopentanol can be prepared.

PREPARATION EXAMPLE 6

Optically active (+)-oxabicyclohexamethanol derivative [Formula (IV): $R^1 = R^2 = CH_3$, $(R)_n = 4\text{-Cl}$]

Preparation of (+)-5-[(4-chlorophenyl)methyl]-2,2-dimethyl-6-oxabicyclo[3.1.0]hexane-1-methanol:

1.42 g (5 mmol) of Ti(O i-Pr) were dissolved in 15 ml of dichloromethane and stirred at −20° C. (dry ice/carbon tetrachloride) under a nitrogen stream. To the mixture was added 1.03 g (5 mmol) of (+)-DET and 1.25 g (5 mmol) of 2-[(4-chlorophenyl)methyl]-5,5-dimethyl-1-cyclopentene-1-methanol [Formula (III): $R^1 = R^2 = CH_3$, $(R)_n = 4\text{-Cl}$]. After stirred at −20° C. for 5 minutes, 6 ml (10 mmol) of a toluene solution of anhydrous TBHP (1.67 mol/l) was added dropwise thereto. The reaction concluded at −20° C. for 1 hour. After stirred at room temperature for 60 minutes, 6 ml of 30% sodium hydroxide-saturated aqueous solution of sodium chloride were added to the resulted mixture and stirred for further 30 minutes After allowed to stand for a while by adding 1 ml of methanol, the formed organic layer was separated. The aqueous layer was extracted with dichloromethane. The separated organic layers were combined, dried with anhydrous sodium sulfate, and concentrated under reduced pressure to yield 1.35 g of a light-yellowish oily product.

The resultant oily product was purified by chromatography on a column of silica gel to obtain 1.16 g (4.35 mmol) of (+)-5-[(4-chlorophenyl)methyl]-2,2-dimethyl-6-oxabicyclo[3.1.0]hexane-1-methanol [(Formula (I): $R^1 = R^2 = CH_3$, $(R)_n = 4\text{-Cl}$].

Yield: 87%

Colorless transparent oil $[\alpha]_D^{20}$ +25.4° (c=1.26, EtOH):91% ee (by HPLC)

$^1H$ NMR(CDCl$_3$); δ 0.9(s,3H),1.10(s,3H),1.0–1.83(m,4H), 2.43(s,1H), 3.0(s,2H), 3.8(d,1H,J=12 Hz), 4.1(d,1H,J=12 Hz), 7.13(m,4H)

IR(neat, ν max); 3400, 2950, 2850, 1482, 1360, 1082, 1010, 836, 780 cm$^{-1}$

PREPARATION EXAMPLE 7

Optically active (+)-oxabicyclohexanemethanol sulfonic acid ester [Formula(V): $R^1=R^2=CH_3$, $(R)_n=$4-Cl, $Y=CH_3$]

Preparation of (+)-5-[(4-chlorophenyl)methyl]-2,2-dimethyl-6-oxabicyclo[3.1.0]hexane-1-methanol methanesulfonic acid ester:

0.84 g (3.15 mmol) of (+)-5-[(4-chlorophenyl) methyl-2,2-dimethyl-6-oxabicyclo [3.1.0]hexane-1-methanol [Formula (IV): $R^1=R^2=CH_3$, $(R)_n=$4-Cl] were dissolved in 10 ml of dichloromethane, followed by adding 0.41 g (3.5 mmol) of methanesulfonyl chloride and 0.3 g (3.5 mmol) of triethylamine were added thereto with stirring under cooling with ice.

The mixture was then stirred under cooling with ice for 1 hour. After conclusion of the reaction was confirmed by TLC, the reaction solution was poured into water and extracted with dichlorometane. The resultant organic layer was washed with aqueous solution of saturated sodium hydrogen carbonate and aqueous common salt liquor. After dried with anhydrous sodium sulfate, the organic layer was concentrated under reduced pressure to yield 1.22 g of a light-yellowish oily product.

The resultant oily product was purified by chromatography on a column of silica gel to obtain 1.02 g (2.96 mmol) of (+)-5-[(4-chlorophenyl)methyl]-2,2-dimethyl-6-oxabicyclo[3.1.0]hexane-1-methanol methanesulfonic acid ester [Formula (V): $R^1=R^2=CH_3$, $(R)_n=$4-Cl, $Y=CH_3$]

Yield: 94%
Colorless transparent oil
$[\alpha]_D^{20}$ +24° (c=1.08, EtOH)
$^1H$ NMR(CDCl$_3$); δ 0.98(s,3H),1.10(s,3H),0.83-2.0 (m,4H),2.93(s,2H),3.07(s,3H),4.37(d,1H,J=12 Hz),4.70(d,1H,J=12 Hz), 7.07(d,2H,J=8 Hz),7.25(d,2H,J=8 Hz)
IR(neat, ν max); 3000, 2940, 2850, 1480, 1350, 1162, 1080, 944, 810 cm$^{-1}$

PREPARATION EXAMPLE 8

Optically active (−)-azolylmethyloxabicyclohexane derivative [Formula (VI): $R^1=R^2=CH_3$, $(R)_n=$4-Cl, $A=N$]

Preparation of (−)-5-[(4-chlorophenyl)methyl]-2,2-dimethyl-(1H-1,2,4-triazol-1-ylmethyl)-6-oxabicyclo[3.1.0]hexane (Compound No. VI - 3):

To 0.12 g (3.0 mmol) of oily 60% sodium hydride washed with hexane was added 5 ml of DMF and stirred at room temperature. 0.21 g (3.0 mmol) of 1,2,4-triazole were then added thereto. After the mixture was stirred for 10 minutes, 2 ml of a DMF solution containing 0.86 g (2.5 mmol) of (−)-5-[(4-chlorophenyl)methyl]-2,2-dimethyl-6-oxabicyclo[3.1.0]hexane-1-methanol methanesulfonic acid ester [Formula (V): $R^1=R^2=CH_3$, $(R)_n=$4-Cl, $Y=CH_3$] was added dropwise thereto.

Thereafter, the mixture was stirred at room temperature for 1 hour and at 40° C. for 4 hours, and the reaction solution was poured into ice water, followed by extracting with ethyl acetate. The resultant organic layer was washed with 1N-hydrochloric acid, saturated aqueous solution of sodium hydrogen carbonate and saturated aqueous salinel solution. After dried with anhydrous sodium sulfate, the organic layer was concentrated under reduced pressure to yield 0.82 g of a light-yellowish oily product.

The resultant oily product was purified by chromatography on a column of silica gel, followed by crystallizing with hexane to obtain 0.77 g (2.42 mmol) of (−)-5-[(4-chlorophenyl)methyl]-2,2-dimethyl-1-(1H-1,2,4-triazol-1-ylmethyl)-6-oxabicyclo[3.1.0]hexane as white crystal [Formula (VI): $R^1=R^2=CH_3$, $(R)_n=$4-Cl, $A=N$].

Yield: 96.8%
$[\alpha]_D^{20}$ −11° (c=1.0, EtOH)
White crystal, m.p. 97°–99° C.
$^1H$ NMR(CDCl$_3$), δ 0.73(s,3H),1.0(s,3H),0.83-2.17 (m,4H),2.93(s,2H),3.07(s,3H),4.33(d,1H,J=16 Hz),4.87(d,1H,J=16 Hz), 7.17(d,2H,J=8 Hz),7.33(d,2H,J=8 Hz),7.93(s,1H), 8.33(s,1H)
IR(KBr, ν max); 3100, 2940, 2850, 1480, 1420, 1260, 1200, 1130, 1084, 1020, 950, 840, 720, 660 cm$^{-1}$ With the same procedure as preparation example 8, except using an imidazole in stead of a 1,2,4-triazole, (−)-5-[(4-chlorophenyl)methyl]-2,2-dimethyl-(1H-imidazol-1-ylmethyl)-6-oxabicyclo[3.1.0]hexane (Compound No. VI - 4) can be prepared.

PREPARATION EXAMPLE 9

Optically active cis-azole derivative [Formula (I): $R^1=R^2=CH_3$, $(R)_n=$4-Cl, $A=N$]

Preparation of (−)-cis-5-[(4-chlorophenyl)methyl]-2,2-dimethyl-1-(1H,-1,2,4-triazol-1-ylmethyl)cyclopentanol:

To 212.4 mg (1.59 mmol) of aluminium chloride was added 5 ml of dimethoxyethane (DME) and stirred at room temperature. To the mixtutre was added 181.6 mg (4.78 mmol) of lithium aluminium hydride and stirred for 30 minutes with elevating the temperature to 50° C. 503.7 mg(1.58 mmol) of (−)-5-[(4-chlorophenyl)methyl]-2,2-dimethyl-1-(1H,1,2,4-triazol-1-ylmethyl)-6-oxabicyclo[3.1.0]hexane, [Formula (VI): $R^1=R^2=CH_3$, $(R)_n=$4-Cl, $A=N$] were added to the mixture and stirred at 50° C. for 1 hour.

The reaction solution was poured into 50 ml of ice water and extracted with ethyl acetate. The separated organic layer was washed with saturated aqueous saline solution. After dried with anhydrous sodium sulfate, the organic layer was concentrated under reduced pressure to yield 550 mg of a yellowish oily product.

The resultant oily product was isolated and purified by chromatography on a column of silica gel to obtain 267.4 mg (0.836 mmol) of (−)-cis-5-[(4-chlorophenyl)-methyl]-2,2-dimethyl-1-(1H-1,2,4-triazol-1-ylmethyl)-cyclopentanol [Formula (I): $R^1=R^2=CH_3$, $(R)_n=$4-Cl, $A=N$].

Yield: 52.9%
White crystal, m.p. 137°–138° C. (recrystallization from n-hexane/ethyl acetate=10/1)
$[\alpha]_D^{20}$ −23.7° (c=10.0, EtOH); 99% ee (by HPLC)
$^1H$ NMR(CDCl$_3$); δ 0.60(s,3H),1.00(s,3H),1.07-1.90(m,5H),2.33(bs,2H),3.53 (s,1H),4.13(s,2H),7.06(d,2H,J=8 Hz),7.25(d,2H,J=8 Hz),8.02 (s,1H),8.25(s,1H)
IR(KBr, ν max); 3250, 2940, 2850, 1480, 1380, 1262, 1200, 1124, 1080, 1002, 840, 800, 720, 670 cm$^{-1}$ With the same procedure as preparation example 9, except using the compound (VI - 4) instead of the compound (VI - 3), (−)-cis-5-[(4-chlorophenyl)methyl]-2,2-dimethyl-1-(1H-imidazol-1-ylmethyl)cyclopentanol can be prepared.

PREPARATION EXAMPLE 10

Optically active (−)-oxabicyclohexamethanol derivative [Formula (IV):$R^1 =R^2 =CH_3$ ,$(R)_n =4$-Cl]

Preparation of (−)-5-[(4-chlorophenyl)methyl]-2,2-dimethyl-6-oxabicyclo[3.1.0]hexane-1-methanol:

1.42 g (5 mmol) of Ti(O i-Pr)were dissolved in 15 ml of dichloromethane and stirred at −20° (dry ice/carbon tetrachloride) under a nitrogen stream. To the mixture was added 1.03 g (5 mmol) of (−)-DET and 1.25 g (5 mmol) of 2-[(4-chlorophenyl)methyl]-5,5-dimethyl-1-cyclopentene-1-methanol [Formula (III): $R^1 =R^2 =CH_3$ ,$(R)_n =4$-CL]. After stirred at −20° C. for 5 minutes, 6 ml (10 mmol) of a toluene solution of anhydrous TBHP (1.67 mol/1) was added dropwise thereto. The reaction concluded at −20° C. for 1 hour. After stirred at room temperature for 60 minutes, 6 ml of 30% sodium hydroxide-saturated aqueous solution of common salt were added to the resulted mixture and stirred for further 30 minutes. After allowed to stand for a while by adding 1 ml of methanol, the formed organic layer was separated. The aqueous layer was extracted with dichloromethane. The separated organic layers were combined, dried with anhydrous sodium sulfate, and concentrated under reduced pressure to yield 1.40 g of a light-yellowish oily product.

The resultant oily product was purified by chromatography on a column of silica gel to obtain 1.16 g (4.35 mmol) of (+)-5-[(4-chlorophenyl)methyl]-2,2-dimethyl-6-oxabicyclo[3.1.0]hexane-1-methanol [Formula (I): $R^1 =R^2 =CH_3$ ,$(R)_n =4$-Cl].

Yield: 81%
Colorless transparent oil
$[\alpha]_D^{20}$ −25.0° (c=1.64, EtOH),:98.8% ee (by HPLC)
$^1H$ NMR (CDCl$_3$); δ 0.9(s,3H),1.10(s,3H),1.0–1.83(m,4H), 2.43(s,1H), 3.0(s,2H), 3.8(d,1H,J=12 Hz), 4.1(d,1H,J=12 Hz), 7.13(m,4H)

IR(neat, ν max); 3400, 2950, 2850, 1482, 1360, 1082, 1010, 836, 780 cm$^{-1}$

PREPARATION EXAMPLE 11

Optically active (−)-oxabicyclohexanemethanol sulfonic acid ester [Formula (V): $R^1 =R^2 =CH_3$ ,$(R)_n =4$-Cl, Y=CH$_3$]

Preparation of (−)-5-[(4-chlorophenyl)methyl]-2,2-dimethyl-6-oxabicyclo[3.1.0]hexane-1-methanol methanesulfonic acid ester: 0.93 g (3.48 mmol) of (−)-5-[(4-chlorophenyl)methyl]-2,2-dimethyl-6-oxabicyclo[3.1.0-]hexane-1-methanol [Formula (IV): $R^1 =R^2 =CH_3$ ,$(R)_n =4$-Cl] were dissolved in 10 ml of dichloromethane, followed by adding 0.44 g (3.8 mmol) of methanesulfonyl chloride and 0.38 g (3.8 mmol) of triethylamine were added thereto with stirring under cooling with ice.

The mixture was then stirred under cooling with ice for 1 hour. After conclusion of the reaction was confirmed by TLC, the reaction solution was poured into water and extracted with dichlorometane. The resultant organic layer was washed with aqueous solution of saturated sodium hydrogen carbonate and aqueous common salt liquor. After dried with anhydrous sodium sulfate, the organic layer was concentrated under reduced pressure to yield 1.27 g of a light-yellowish oily product.

The resultant oily product was purified by chromatography on a column of silica gel to obtain 1.14 g (3.3 mmol) of (−)-5-[(4-chlorophenyl)methyl]-2,2-dimethyl-6-oxabicyclo[3.1.0]hexane-1-methanol methanesulfonic acid ester [Formula (V): $R^1 =R^2 =CH_3$ ,$(R)_n =4$-Cl, Y=CH$_3$ ]

Yield: 95%
Colorless transparent oil
$[\alpha]_D^{20}$ −24.5° (c=1.2, EtOH)
$^1H$ NMR(CDCl$_3$ ); δ 0.98(s,3H),1.10(s,3H),0.83–2.0(m,4H),2.93(s,2H),3.07 (s,3H),4.37(d,1H,J=12 Hz),4.70(d,1H,J=12 Hz),7.07(d,2H, J=8 Hz),7.25(d,2H,J=8 Hz)

IR(neat,ν max); 3000, 2940, 2850, 1480, 1350, 1162, 1080, 944, 810 cm$^{-1}$

PREPARATION EXAMPLE 12

Optically active (+)-azolylmethyloxabicyclohexane derivative [Formula (VI): $R^1 =R^2 =CH_3$ ,$(R)_n =4$-Cl, A=N]

Preparation of (+)-5-[(4-chlorophenyl)methyl]-2,2-dimethyl-(1H-1,2,4-triazol-1-ylmethyl)-6-oxabicyclo-[3.1.0]hexane (Compound No. VI - 5):

To 0.14 g (3.5 mmol) of oily 60% sodium hydride washed with hexane was added 5 ml of dimethylformamide (DMF) and stirred at room temperature. 0.25 g (3.6 mmol) of 1,2,4-triazole were then added thereto. After the mixture was stirred for 10 minutes, 2 ml of a DMF solution containing 1.03 g (3.0 mmol) of (−)-5-[(4-chlorophenyl)methyl]-2,2-dimethyl-6-oxabicyclo[3.1.0]-hexane-1-methanol methanesulfonic acid ester [Formula (V): $R^1 =R^2 =CH_3$ ,$(R)_n =4$-Cl, Y=CH$_3$] was added dropwise thereto.

Thereafter, the mixture was stirred at room temperature for 1 hour and at 40 ° C. for 4 hours, and the reaction solution was poured into ice water, followed by extracting with ethyl acetate. The resultant organic layer was washed with 1N-hydrochloric acid, saturated aqueous solution of sodium hydrogen carbonate and saturated aqueous saline solution. After dried with anhydrous sodium sulfate, the organic layer was concentrated under reduced pressure to yield 1.05 g of a light-yellowish oily product.

The resultant oily product was purified by chromatography on a column of silica gel, followed by crystallizing with hexane to obtain 0.89 g (2.8 mmol) of (+)-5-[(4-chlorophenyl)methyl]-2,2-dimethyl-1-(1H-1,2,4-triazol-1-ylmethyl)-6-oxabicyclo[3.1.0]hexane as white crystal [Formula (VI): $R^1 =R^2 =CH_3$ ,$(R)_n =4$-Cl, A=N].

Yield: 93.3%
$[\alpha]_D^{20}$ +12° (c=1.0, EtOH)
White crystal, m.p. 97°-99° C.
$^1H$ NMR(CDCl$_3$); δ 0.73(s,3H),1.0(s,3H),0.83–2.17(m,4H),2.93(s,2H),3.07 (s,3H),4.33(d,1H,J=16 Hz),4.87(d,1H,J=16 Hz),7.17(d,2H, J=8 Hz),7.33(d,2H,J=8 Hz),7.93(s,1H),8.33(s,1H)

IR(KBr, ν max); 3100, 2940, 2850, 1480, 1420, 1260, 1200, 1130, 1084, 1020, 950, 840, 720, 660 cm$^{-1}$ With the same procedure as preparation example 12, except using an imidazole in stead of a 1,2,4-triazole, triazole, (+)-5-[(4-chlorophenyl)methyl]-2,2-dimethyl-(1H-imidazol-1-ylmethyl)-6-oxabicyclo[3.1.0]hexane (Compound No. VI - 6) can be prepared.

PREPARATION EXAMPLE 13

Optically active cis-azole derivative [Formula (I):$R^1 = R^2 = CH_3$ ,$(R)_n = 4$-Cl, A=N]

Preparation of (+)-cis-5-[(4-chlorophenyl)methyl]-2,2-dimethyl-1-(1H-1,2,4-triazol-1-ylmethyl)cyclopentanol To 0.27 g (2.0 mmol) of aluminium chloride was added 5 ml of dimethoxyethane (DME) and stirred at room temperature. To the mixture was added 0.23 g (6.1 mmol) of lithium aluminium hydride and stirred for 30 minutes with elevating the temperature to 50° C. 0.64 g (2.0 mmol) of (+)-5-[(4-chlorophenyl)methyl]-2,2-dimethyl-1-(1H-1,2,4-triazol-1-ylmethyl)-6-oxabicyclo[3.1.0]hexane [Formula (VI): $R^1 = R^2 = CH_3$ ,$(R)_n = 4$-Cl, A=N] were added to the mixture and stirred at 50° C. for 1 hour.

The reaction solution was poured into 50 ml of ice water and extracted with ethyl acetate. The separated organic layer was washed with saturated aqueous saline solution. After dried with anhydrous sodium sulfate, the organic layer was concentrated under reduced pressure to yield 0.72 g of a yellowish oily product.

The resultant oily product was isolated and purified by chromatography on a column of silica gel to obtain 0.36 g (1.13 mmol) of (+)-cis-5-[(4-chlorophenyl)methyl]-2,2-dimethyl-1-(1H-1,2,4-triazol-1ylmethyl)cyclopentanol [Formula (I): $R^1 = R^2 = CH_3$ ,$(R)_n = 4$-Cl, A=N].

Yield: 56.5%

White crystal, m.p. 137°-138° C. (recrystallization from n-hexane/ethyl acetate=10/1)

$[\alpha]_D^{20}$ +23.7° (c=10.0, EtOH):99% ee (by HPLC)

$^1$H NMR(CDCl$_3$); δ 0.60(s,3H),1.00(s,3H), 1.07-1.90(m,5H),2.33(bs,2H), 3.53(s,1H),4.13(s,2H),7.06(d,2H,J=8 Hz),7.25(d,2H,J=8 Hz), 8.02(s,1H),8.25(s,1H)

IR(KBr, ν max); 3250, 2940, 2850, 1480, 1380, 1262, 1200, 1124, 1080, 1002, 840, 800, 720, 670 cm$^{-1}$ With the same procedure as preparation example 13, except using the compound (VI - 6) instead of the compound (VI - 5), (+)-cis-5-[(4-chlorophenyl)methyl]-2,2-dimethyl-1-(1H-imidazol-1-ylmethyl)cyclopentanol can be prepared.

PREPARATION EXAMPLE 14

Optically active (+)-oxabicyclohexanemethanol derivative [Formula(IV): $R^1 = R^2 = CH_3$ ,$(R)_n = 4$-Cl]

Preparation of (+)-5-[(4-chlorophenyl)methyl]-2,2-dimethyl-6-oxabicyclo[3.1.0]hexane methanol:

15 ml of dichloromethane were placed in a 3-neck flask (50 ml) and stirred at −40° C. (dry ice/acetone) under a nitrogen stream. After 200 mg of Molecular Sieve 4A (powdered, activated molecular sieves; Aldrich Co.) with stirring, 28.4 mg (0.1 mmol; 5 mol %) of Ti(O i-Pr)$_4$, 31 mg (0.15 mmol; 7.5 mol %) of (+)-DET and 500 mg (2.0 mmol) of 2-[(4-chlorophenyl)methyl]-5,5-dimethyl-1-cyclopentene-1-methanol [Formula (III): $R^1 = R^2 = CH_3$ ,$(R)_n = 4$-Cl] were added thereto and the resultant mixture was stirred at −40° C. for 10 minutes. Thereafter 2.4 ml (4.0 mmol) of a toluene solution of anhydrous TBHP (1.67 mol/l) were added dropwise so as not to elevate the temperature to −40° C.

After allowed to react at −40° C. for 5 hours, 20 ml of water were added thereto, followed by stirring for 30 minutes. Thereafter, 5 ml of 30% sodium hydroxide saturated aqueous common salt liquor were added to the mixture, followed by stirring further 30 minutes. After allowed to stand for a while by adding 1 ml of methanol, the formed organic layer was separated. The aqueous layer was extracted with dichloromethane. The separated organic layers were combined, dried with anhydrous sodium sulfate, and concentrated under reduced pressure to yield 0.63 g of a colorless transparent oily product.

The resultant product was purified by chromatography on a column of silica gel to obtain 0.46 g (1.7 mmol) of (+)-5-[(4-chlorophenyl)methyl]-2,2-dimethyl-6-oxabicyclo[3.1.0]hexane-1-methanol [Formula (IV): $R^1 = R^2 = CH_3$ ,$(R)_n = 4$-Cl].

Yield: 81%

Colorless transparent oil $[\alpha]_D^{20}$ +18° (c=1.5, EtOH):64% ee (by HPLC)

$^1$H NMR (CDCl$_3$); δ 0.9(s,3H),1.10(s,3H),1.0~1.83(m,4H), 2.43(s,1H), 3.0(s,2H), 3.8(d,1H,J=12 Hz), 4.1(d,1H,J=12 Hz),7.13(m,4H)

IR(neat, ν max); 3400, 2950, 2850, 1482, 1360, 1082, 1010, 836, 780 cm$^{-1}$

PREPARATION EXAMPLE 15

Optically active (+)-oxabicyclohexanemethanol derivative [Formula (IV): $R^1 = R^2 = CH_3$ ,$(R)_n = 4$-Cl]

Preparation of (+)-5-[(4-chlorophenyl)methyl]-2,2-dimethyl-6-oxabicyclo[3.1.0]hexane-1-methanol:

5 ml of dichloromethane were placed in a 3-neck flask (50 ml) and stirred at −40° C. (dry ice/acetonitril) under a nitrogen stream. After 200 mg of Molecular Sieve 4A (powdered, activated molecular sieves; Aldrich Co.) with stirring, 28.4 mg (0.1 mmol; 10 mol %) of Ti(O i-Pr)$_4$, 32 mg (0.15 mmol; 15 mol %) of (+)-DET and 250 mg (1.0 mmol) of 2-[(4-chlorophenyl)methyl]-5,5-dimethyl-1-cyclopentene-1-methanol [Formula (III): $R^1 = R^2 = CH_3$ ,$(R)_n = 4$-Cl] were added thereto and the resultant mixture was stirred at −40° C. for 10 minutes. Thereafter 1.2 ml (2.0 mmol) of a toluene solution of anhydrous TBHP (1.67 mol/l) were added dropwise so as not to elevate the temperature to −40° C.

After allowed to react at −40° C. for 5 hours, 20 ml of water were added thereto, followed by stirring for 30 minutes. Thereafter, 5 ml of 30% sodium hydroxide-saturated aqueous saline solution were added to the mixture, followed by stirring further 30 minutes. After allowed to stand for a while with adding 1 ml of methanol, the formed organic layer was separated. The aqueous layer was extracted with dichloromethane. The separated organic layers were combined, dried with anhydrous sodium sulfate, and concentrated under reduced pressure to yield 0.28 g of a colorless transparent oily product.

The resultant product was purified by chromatography on a column of silica gel to obtain 0.22 g (1.7 mmol) of (+)-5-[(4-chlorophenyl)methyl]-2,2-dimethyl-6-oxabicyclo[3.1.0]hexane-1-methanol [Formula (IV): $R^1 = R^2 = CH_3$ ,$(R)_n = 4$-Cl].

Yield: 82%

Colorless transparent oil $[\alpha]_D^{20}$ +23.2° (c=1.5, EtOH):80% ee (by HPLC)

PREPARATION EXAMPLE 16

Optically active (+)-oxabicyclohexanemethanol derivative [Formula (IV): $R^1 = R^2 = CH_3, (R)_n = 4\text{-}Cl$]

Preparation of (+)-5-[(4-chlorophenyl)methyl]-2,2-dimethyl-6-oxabicyclo[3.1.0]hexane-1-methanol:

5 ml of dichloromethane were placed in a 3-neck flask (50 ml) and stirred at −20° C. (dry ice/carbon tetrachloride) under a nitrogen stream. After 200 mg of Molecular Sieve 4A (powdered, activated molecular sieves; Aldrich Co.) with stirring, 28.4 mg (0.1 mmol; 10 mol %) of Ti(O i-Pr)$_4$, 33.7 mg (0.16 mmol;16 mol %) of (+)-DET and 250 mg (1.0 mmol) of 2-[(4-chlorophenyl)-methyl]-5,5-dimethyl-1-cyclopentene-1-methanol [Formula (III): $R^1 = R^2 = CH_3, (R)_n = 4\text{-}Cl$] were added thereto and the resultant mixture was stirred at −20° C. for 10 minutes. Thereafter 1.2 ml (2.0 mmol) of a toluene solution of anhydrous TBHP (1.67 mol/1) were added dropwise so as not to elevate the temperature to −20° C.

After allowed to react at −20° C. for 2 hours, 20 ml of water were added thereto, followed by stirring for 30 minutes. Thereafter, 5 ml of 30% sodium hydroxide-saturated aqueous saline solution were added to the mixture, followed by stirring further 30 minutes. After allowed to stand for a while with adding 1 ml of methanol, the formed organic layer was separated. The aqueous layer was extracted with dichloromethane. The separated organic layers were combined, dried with anhydrous sodium sulfate, and concentrated under reduced pressure to yield 0.32 g of a colorless transparent oily product.

The resultant product was purified by chromatography on a column of silica gel to obtain 206.4 mg (0.77 mmol) of (+)-5-[(4-chlorophenyl)methyl]-2,2-dimethyl-6-oxabicyclo[3.1.0]hexane-1-methanol [Formula (IV): $R^1 = R^2 = CH_3, (R)_n = 4\text{-}Cl$].

Yield: 77%

Colorless transparent oil $[\alpha]_D^{20}$ +12.6° (c=1.2, EtOH): 48% ee (by HPLC)

PREPARATION EXAMPLE 17

Optically active (+)-oxabicyclohexanemethanol derivative [Formula (IV): $R^1 = R^2 = CH_3, (R)_n = 4\text{-}Cl$]

Preparation of (+)-5-[(4-chlorophenyl)methyl]-2,2-dimethyl-6-oxabicyclo[3.1.0]hexane-1-methanol:

5 ml of dichloromethane were placed in a 3-neck flask (50 ml) and stirred at 0° C. under a nitrogen stream. After 200 mg of Molecular Sieve 4A (powdered, activated molecular sieves; Aldrich Co.) with stirring, 28.4 mg (0.1 mmol;10 mol %) of Ti(O i-Pr)$_4$, 32 mg (0.15 mmol;15mol %) of (+)-DET and 250 mg (1.0 mmol) of 2-[(4-chlorophenyl)methyl]-5,5-dimethyl-1-cyclopentene-1-methanol [Formula (III): $R^1 = R^2 = CH_3, (R)_n = 4\text{-}Cl$] were added thereto and the resultant mixture was stirred at 0° C. for 10 minutes. Thereafter 1.2 ml (2.0 mmol) of a toluene solution of anhydrous TBHP (1.67mol/1) were added dropwise so as not to elevate the temperature to 0° C.

The reaction was completed in 30 minutes. After 20 ml of water were added and stirred at room temperature for 30 minutes, 5 ml of 30% sodium hydroxide-saturated aqueous saline solution were added to the mixture, followed by stirring further 30 minutes. After allowed to stand for a while with adding 1 ml of methanol, the resulted organic layer was separated. The aqueous layer was extracted with dichloromethane. The separated organic layers were combined, dried with anhydrous sodium sulfate, and concentrated under reduced pressure to yield 0.28 g of a colorless transparent oily product.

The resultant product was purified by chromatography on a column of silica gel to obtain 196.4 mg (0.74 mmol) of (+)-5-[(4-chlorophenyl)methyl]-2,2-dimethyl-6-oxabicyclo[3.1.0]hexane-1-methanol [Formula (IV): $R^1 = R^2 = CH_3, (R)_n = 4\text{-}Cl$].

Yield: 74%

Colorless transparent oil $[\alpha]_D^{20}$ +7° (c=1.5, EtOH): 20% ee (by HPLC)

PREPARATION EXAMPLE 18

Optically active (+)-oxabicyclohexanemethanol derivative [Formula (IV): $R^1 = R^2 = CH_3, (R)_n = 4\text{-}Cl$]

Preparation of (+)-5-[(4-chlorophenyl)methyl]-2,2-dimethyl-6-oxabicyclo[3.1.0]hexane-1-methanol:

5 ml of dichloromethane were placed in a 3-neck flask (50 ml) and stirred at −40° C. (dry ice/acetonitril) under a nitrogen stream. After 200 mg of Molecular Sieve 4A (powdered, activated molecular sieves; Aldrich Co.) with stirring, 29.8 mg (0.105 mmol;7 mol %) of Ti(O i-Pr)$_4$, 33 mg (0.15 mmol; 10 mol %) of (+)-DET and 376 mg (1.5 mmol) of 2-[(4-chlorophenyl)methyl]-5,5-dimethyl-1-cyclopentene-1-methanol [Formula (III): $R^1 = R^2 = CH_3, (R)_n = 4\text{-}Cl$] were added thereto and the resultant mixture was stirred at −40° C. for 10 minutes. Thereafter 1.2 ml (2.0 mmol) of a toluene solution of anhydrous TBHP (1.67 mol/1) were added dropwise so as not to elevate the temperature to −40° C.

After allowed to react at −40° for 5 hours, 20 ml of water were added thereto, followed by stirring for 30 minutes. Thereafter, 5 ml of 30% sodium hydroxide-saturated aqueous saline solution were added to the mixture, followed by stirring further 30 minutes. After allowed to stand for a while with adding 1 ml of methanol, the resulted organic layer was separated. The aqueous layer was extracted with dichloromethane. The separated organic layers were combined, dried with anhydrous sodium sulfate, and concentrated under reduced pressure to yield 0.45 g of a colorless transparent oily product.

The resultant product was purified by chromatography on a column of silica gel to obtain 330.6 mg (1.24 mmol) of (+)-5-[(4-chlorophenyl)methyl]-2,2-dimethyl-6-oxabicyclo[3.1.0]hexane-1-methanol [Formula (IV): $R^1 = R^2 = CH_3, (R)_n = 4\text{-}Cl$].

Yield: 82.7%

Colorless transparent oil $[\alpha]_D^{20}$ +23.5° (c=1.5, EtOH):72% ee (by HPLC)

FORMULATION EXAMPLE 1

Dust

|  | Parts by weight |
| --- | --- |
| Compound (VI) | 3 |
| Clay | 40 |
| Talc | 57 |

The above-mentioned ingredients were mixed to prepare a dust.

FORMULATION EXAMPLE 2

Wettable Powder

|  | Parts by weight |
|---|---|
| Compound (VI) | 50 |
| Ligninsulfonate | 5 |
| Alkylsulfonate | 3 |
| Diatomaceous earth | 42 |

The above-mentioned ingredients were mixed to prepare a wettable powder.

FORMULATION EXAMPLE 3

Granule

|  | Part by weight |
|---|---|
| Compound (VI) | 5 |
| Bentonite | 43 |
| Clay | 45 |
| Ligninsulfonate | 7 |

The above-mentioned ingredients were mixed and kneaded with adding water thereto. The mixture was gnalurated by means of an extrusion granulating machine, followed by drying to obtain granules.

FORMULATION EXAMPLE 4

Emulsion

|  | Parts by weight |
|---|---|
| Compound (VI) | 20 |
| Polyoxyethylene alkyl aryl ether | 10 |
| Polyoxyethylnene sorbitan monolaurate | 3 |
| Xylene | 67 |

The above mentioned ingredients were mixed and dissolved to obtain an emulsion.

TEST EXAMPLE

Antimicrobial test against various microorganisms:

This example shows results of the following antimicrobial test of optically active (−)-azolylmethyloxabicyclohexane derivative (formula (VI): $R^1 = R^2 = CH_3$, $(R)_n = 4\text{-}Cl$, $A = N$) prepared in Preparation Example 8 against various kinds of plant disease microorganisms.

Method

The compound of this invention was dissolved in dimethylsulfoxide in a suitable concentration. 0.6 ml of the solution was well mixed with 60 ml of a PAS culture medium at about 60° C. in a 100 ml conical flask, and the resultant mixture was poured into Petri dishes and was caused to coagulate, by which plate culture media containing the compound of this invention were obtained.

On the other hand, plate culture media on which test microorganisms were previously cultured were punched by a cork borer so as to have a diameter of 4 mm, followed by inoculating on the above-mentioned plate culture medium. After inoculation was carried out, they were incubated for 1-3 days at a preferable temperature for each microorganism, and growth of microorganisms was obserbed by measuring the diameter of the colony. Hyphae elongation inhibitory rates were determined respectively in accordance with the below-described equation.

$$R = 100\ (dc - dt)/dc$$

wherein

R = Hyphae elongation inhibitory rate (%)

dc = Diameter of colony on the non-treated plate culture medium dt = Diameter of colony on the plate culture medium containing the tested compound Test results were ranked in five stages by the following ranking system. The results are shown in Table 1.

5 ... at least 90%-100%
4 ... at least 70% but lower than 90%
3 ... at least 40% but lower than 70%
2 ... at least 20% but lower than 40%
1 ... lower than 20%

TABLE 1

| Test fungus | Biocidal activity (concentration: 100 μg/ml) |
|---|---|
| Pyricularia oryzae | 5 |
| Cochliobolus miyabeanus | 5 |
| Gibberella fujikuroi | 5 |
| Helminthosporium sigmoideum | 5 |
| Rhizoctonia solani | 3 |
| Botrytis cinerea | 5 |
| Sclerotinia sclerotiorum | 5 |
| Fusarium oxysporum f.sp. niveum | 5 |
| Fusarium oxysporum f.sp. 5 cucumerinum | - |
| Fusarium oxysporum f.sp. raphani | 5 |
| Colletotrichum lagenarium | 4 |
| Cercospola beticola | 5 |
| Cercospore kikuchii | 4 |
| Monilinia fructicola | 5 |
| Alternaria kikuchiana | 4 |
| Alternaria mali | 5 |
| Glomerella cingulata | 5 |

We claim:

1. An azolylmethyloxabicyclohexane derivative represented by the formula (VI)

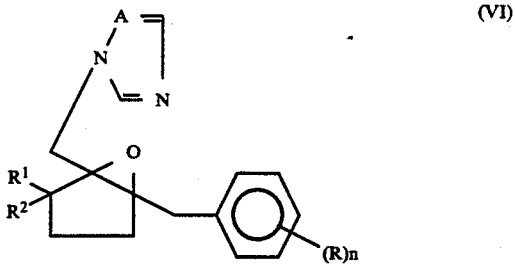

(VI)

wherein $R^1$ and $R^2$ denote each a hydrogen atom or a $C_1$-$C_5$ alkyl group, R denotes a halogen atom a nitro group, a cyano group, a $C_1$-$C_5$ alkyl group, a $C_1$-$C_5$ haloalkyl group or a phenyl group, A denotes a nitrogen atom, and n stands for 0 or an integer of 1-5.

2. The azolylmethyloxabicyclohexane derivative of claim 1, wherein $R^1$ is $CH_3$, $R^2$ is $CH_3$, R is 4-CL, and n is 1.

3. The azolylmethyloxabicyclohexane derivative of claim 1 which is (+)-5-[(4-chlorophenyl)methyl]-2,2-dimethyl-1-(1H-1,2,4-triazol-1-ylmethyl)-6oxabicyclo[3.1.0]hexane.

4. The azolylmethyloxabicyclohexane derivative of claim 1 which is (−)-5-[(4-chlorophenyl)methyl]-2,2- dimethyl-1-(1H,-1,2,4-triazol-1-ylmethyl)-6-oxabicyclo[3.1.0]hexane.

5. A fungicidal composition comprising an effective amount of an azolylmethyloxabicyclohexane derivative represented by the following formula together with an inert carrier or other adjuvants

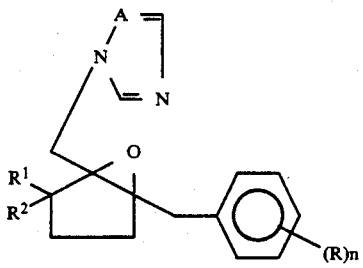

wherein $R^1$, $R^2$, R and n have the same meanings as defined in claim 1, A denotes a nitrogen atom.

6. The fungicidal composition of claim 5, wherein $R^1$ is $CH_3$, $R^2$ is $CH_3$, R is 4-Cl, and n is 1.

7. The fungicidal composition of claim 5, wherein the azolylmethyloxabicyclohexane derivative is (—)-5--[(4-chlorophenyl)methyl]-2,2-dimethyl-1-(1H)-1,2,4-triazol-1-ylmethyl)-6-oxabicyclo[3.1.0]hexane.

* * * * *